(12) United States Patent
Payne et al.

(10) Patent No.: US 7,288,532 B1
(45) Date of Patent: Oct. 30, 2007

(54) MODIFIED CHITOSAN POLYMERS AND ENZYMATIC METHODS FOR THE PRODUCTION THEREOF

(75) Inventors: Gregory F. Payne, Hunt Valley, MD (US); Guneet Kumar, Ellicott City, MD (US)

(73) Assignees: The University of Maryland Biotechnology Institute, Rockville, MD (US); The University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 09/763,324

(22) PCT Filed: Aug. 20, 1999

(86) PCT No.: PCT/US99/19106

§ 371 (c)(1),
(2), (4) Date: Jun. 18, 2001

(87) PCT Pub. No.: WO00/11038

PCT Pub. Date: Mar. 2, 2000

Related U.S. Application Data

(60) Provisional application No. 60/097,709, filed on Aug. 21, 1998.

(51) Int. Cl.
C08G 8/00 (2006.01)
C12P 19/04 (2006.01)

(52) U.S. Cl. ............... 514/55; 435/68.1; 435/72; 435/74; 435/101; 527/200; 527/206; 527/303; 536/20; 536/55.1; 536/55.3; 536/127

(58) Field of Classification Search .............. 536/20; 435/84
See application file for complete search history.

(56) References Cited

U.S. PATENT DOCUMENTS 5,147,698 A * 9/1992 Cole ........................ 428/40
5,340,483 A * 8/1994 Payne et al. ............. 210/632
5,422,116 A * 6/1995 Yen et al. ................ 424/427
5,474,989 A * 12/1995 Hashimoto et al. ......... 514/55

OTHER PUBLICATIONS

JP 09239396 A, XP-002221719, (Abstract), *Derwent Publications Ltd.*, Section Ch, Week 9744, AN 1997-507214, Sep. 16, 1997.
S. Wada et al., "Removal of Phenols and Aromatic Amines from Wastewater by a Combination Treatment With Tyrosinase and a Coagulant," *Biotechnology and Bioengineering*, 45:304-309 (1995), XP-001119098.
R. Muzzarelli et al., "Tyrosinase-mediated quinone tanning of chitinous materials," *Carbohydrate Polymers*, 24:295-300 (1994), XP 000645409.
G. Payne et al., "Tyrosinase Reaction/Chitosan Adsorption for Selectively Removing Phenols from Aqueous Mixtures," *Biotechnology and Bioengineering*, 40(9):1011-1018 (1992), XP 000306318.
English Translation of JP 9 239 396 (1997).

* cited by examiner

*Primary Examiner*—Frederick Krass
(74) *Attorney, Agent, or Firm*—Jeffrey I. Auerbach; Edell, Shapiro & Finnan, LLC

(57) ABSTRACT

The present invention is directed to homogeneous phase enzyme-catalyzed processes for producing modified chitosan polymers or oligomers. An enzyme is reacted with a phenolic substrate in the presence of a chitosan polymer or oligomer to produce a modified chitosan polymer or oligomer. The invention also includes modified chitosan polymers or oligomers produced by the novel processes, in particular modified chitosan polymers or oligomers having useful functional properties, such as base solubility and/or high viscosity.

36 Claims, 6 Drawing Sheets

7.0　　　　6.0

MODIFIED CHITOSAN POLYMERS AND ENZYMATIC METHODS FOR THE PRODUCTION THEREOF

This application is the U.S. national stage of international application No. PCT/US99/19106, filed Aug. 20, 1999, which claims priority to U.S. provisional patent application No. 60/097,709, filed Aug. 21, 1998. Both applications are incorporated herein by reference.

1. FIELD OF THE INVENTION

The present invention relates to enzyme-catalyzed modification of natural oligomers and polymers, and in particular, to homogeneous-phase processes for modifying the natural polymer chitosan by reaction in the presence of an enzyme and one or more phenolic compounds. The invention also relates to new modified chitosan polymers and oligomers having useful functional properties.

2. BACKGROUND OF THE INVENTION

Modification of both natural and synthetic polymers is an important method of creating new polymeric species with useful properties. For naturally occurring polymers, such modifications offer the possibility of producing polymers with the desired functional properties, while avoiding the expense and potential environmental costs associated with polymer synthesis based on petrochemical starting materials. Thus, for example, the most abundant natural polymer, cellulose, is widely used in modified forms, such as the carboxyalkylated and hydroxyalkylated derivatives.

While cellulose and its derivatives enjoy widespread usage, other natural and abundant polysaccharide polymers have been relatively under-exploited. One polymer derived from natural sources and offering potentially useful properties is chitosan. Chitosan is obtained by N-deacetylation of chitin, $(C_8H_{13}NO_5)_n$, a glucosamine polysaccharide that is structurally similar to cellulose. Chitin is a principal component of the shells of crustaceans, and is also found in other natural sources such as some insects, fungi, algae and yeast. Deacetylation of chitin by well-known methods such as those described in U.S. Pat. Nos. 4,282,351, 4,368,322 and 4,835,265, yields chitosan (Ia).

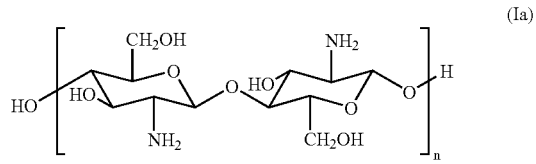

(Ia)

Chitosan is a linear polymer of glucosamine units. Structurally, it is distinguished from cellulose by the presence of the primary amine group. Chitosan is available commercially in various grades and average molecular weights (e.g., Sigma®, Aldrich®).

The presence of amine groups in chitosan confers interesting and potentially useful chemical and physical properties on the polymer. Although chitosan is not water soluble under neutral or alkaline conditions, under mildly acidic conditions (pH less than about 6) the amine groups are protonated and the polycationic polymer becomes water soluble (Ib). At neutral and alkaline pH, the amine groups are deprotonated and the neutral chitosan polymer is water-insoluble (Ia). The protonation-deprotonation, and accompanying change in water solubility, are reversible processes.

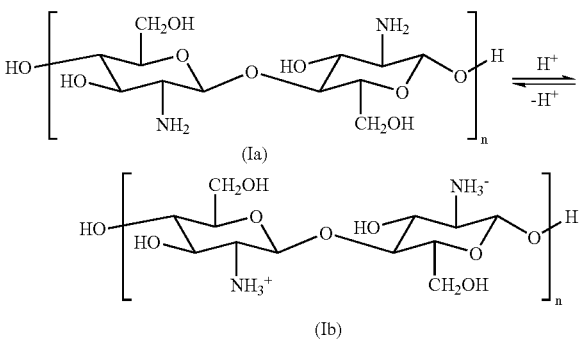

The failure to fully exploit these natural polymers lies, in part, on a lack of clean, effective and versatile processes to modify the polymers to provide needed functional properties. One such functional property is water solubility. Water-soluble polymers are becoming increasingly important compounds useful in a broad range of applications. Their importance lies, in part, in their ability to function in environmentally "friendly" ways. Only relatively few polymers, however, whether natural or synthetic, are water-soluble. The most abundant natural polymers, for example, the polysaccharides cellulose and chitin, are linear polymers with poor water solubility. Although chitosan has substantial solubility in aqueous solution, it is soluble only at low pH. In neutral and basic aqueous solutions, chitosan is essentially insoluble.

Several approaches are possible to solubilize water-insoluble natural polymers. One approach is simply to reduce the polymer's average molecular weight by breaking up polymer chains into smaller chains. Such a molecular weight reduction approach is often impractical, as the resultant polymer may lose desirable physical or biological properties.

A more practical approach is to chemically modify natural polymers to add enough hydrophilic or charged side groups to confer on the polymer the desired degree of water solubility. For example, whereas natural cellulose is insoluble in water, its carboxylated derivatives such as carboxymethylcellulose are an important class of water-soluble natural polymers. Unfortunately, polymer modification reactions typically employ reagents whose use presents environmental problems. A common scheme for the carboxymethylation of cellulose, for example, uses the chlorinated reagent chloroacetic acid, a highly toxic and corrosive chlorinated compound. The potential environmental and safety problems are further exacerbated when the polymeric starting material is itself a synthetic polymer rather than a natural polymer, since such polymers are typically produced using organic solvents and petrochemical-based monomers, the widespread use of which creates additional environmental concerns.

Several schemes for the chemical modification of chitosan have been reported. Carboxymethylation of chitosan can be achieved by treatment with chloroacetic acid (hydroxy nucleophilic reaction), as is done with cellulose, or by reduction of a chitosan glyoxylate (amino nucleophilic reaction) with sodium cyanoborohydride. Muzzarelli et al., "N-(carboxymethylidene)chitosans and N-(carboxymethyl)chitosans: Novel Chelating Polyampholytes Obtained from Chitosan Glyoxylate," Carbohydrate Research, 107, 199-

214 (1982). The N-(carboxymethyl)chitosan products reportedly are soluble in aqueous solutions over a range of pH values. Similarly, soluble carbohydrate derivatives of chitosan have been reported by a reductive alkylation process, again using sodium cyanoborohydride. Yalpani et al., "Some Chemical and Analytical Aspects of Polysaccharide Modifications. 3. Formation of Branched-Chain, Soluble Chitosan Derivatives", Macromolecules, 17, 272-281 (1984). Other soluble chitosan derivatives are known. For example, U.S. Pat. No. 5,378,472 discloses a 5-methylpyrrolidinone chitosan that is reportedly soluble in aqueous alkaline solution. Although these chemical modification approaches can yield chitosan derivatives with altered functional properties (e.g., base solubility), the reagents used to achieve these modifications (e.g., chloroacetic acid and sodium cyanoborohydride) have undesirable properties with respect to health and safety. Moreover, an effective, versatile method of modifying chitosan to provide other useful functional properties is also needed.

One promising approach to producing modified natural polymers is to make use of clean and selective enzymatic reactions. Such reactions could be used, for example, to add hydrophilic side groups or charged groups to polymers to confer enhanced water solubility. Other side groups could also be added in enzyme-catalyzed reactions to change the physical and chemical properties of the polymer. Enzyme modification potentially offers a number of advantages over conventional chemical modification. Enzyme reactions typically do not involve the use of highly reactive reagents, thus avoiding many potential health and safety hazards. In addition, enzyme reactions can be highly selective, and such selectivity can be exploited to eliminate the number of reaction steps necessary to produce the desired product, e.g., by eliminating the need for wasteful protection and deprotection steps.

Some groups have reported successful enzyme-based polymer modifications. In one approach, hydrolytic enzymes are used under non-aqueous conditions to catalyze reactions such as condensation or transesterification. Bruno et al. has reported the transesterification of a caprate group onto amylose, using a protease in an isooctane solvent. Bruno et al., "Enzymatic modification of insoluble amylose in organic solvents," Macromolec., 28:8881-8883 (1995). This approach, however, is subject to severe steric limitations. The reaction mechanism involves formation of an acyl-enzyme intermediate, which undergoes nucleophilic attack at the enzyme's active site, requiring both the acyl intermediate and the polymeric substrate to bind to the enzyme active site. Because of these steric limitations, such reactions, while selective, are quite slow.

In another approach, the above-mentioned steric limitations are eliminated by using a two-step reaction. In a first reaction, the enzyme and substrate react to generate a reactive intermediate species. The intermediate, non-enzyme-bound species diffuses freely through the reaction solvent and reacts remotely with the polymer surface. This approach has been used to graft phenols onto lignin polymers, using a peroxidase. Popp et al., "Incorporation of p-cresol into lignins via peroxidase-catalyzed copolymerization in nonaqueous media," Enzyme Microb. Technol., 13:964-968 (1991); Blinkovsky et al., "Peroxidase-catalyzed synthesis of lignin-phenol copolymers," J. Polym. Sci., 31:1839-1846 (1993). Similarly, this approach has been used to enzymatically create epoxide groups in polybutadiene, using a lipase with hydrogen peroxide to generate a reactive peroxycarboxylic acid intermediate. Jarvie et al., "Enzymatic epoxidation of polybutadiene," Chem. Comm., 177-178 (1998).

Other work has focused on the use of chitosan films or gels in enzyme-catalyzed heterogeneous phase water treatment applications. For example, U.S. Pat. No. 5,340,483 discloses a method of selectively removing phenolic components in wastewater mixtures by reacting the phenolic compound with the enzyme tyrosinase in the presence of chitosan. Enzymes such as tyrosinases, phenol oxidases and polyphenol oxidases are known to react with a wide variety of phenolic compounds. Without wishing to be bound by theory, it is believed that these enzymes act to reduce the phenol to a reactive ortho quinone, as shown in (II).

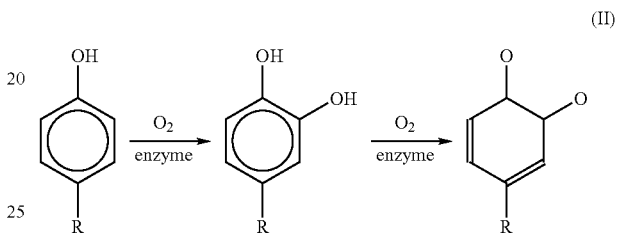

(II)

Quinones in turn react with the chitosan film or gel to form a tightly-bound chemisorbed species, thereby effectively removing the phenol from solution by an enzyme-catalyzed chitosan reaction. Such reaction schemes have important applicability to wastewater treatment and waste management.

Efforts to exploit tyrosinase-catalyzed reactions to create chitosan derivatives with important functional properties have been reported. Payne et al., "Enzyme-based polymer modification: Reaction of phenolic compounds with chitosan films," Polymer, 37, 4643-4648 (1996). These modification approaches employ insoluble chitosan films, and this approach suffers because only the surface of the chitosan gel or film is exposed to the quinone intermediate in this heterogeneous phase process. Other heterogeneous-phase chitosan-tyrosinase reaction schemes are described, for example, in Lenhart et al., "Enzymatic Modification of Chitosan by Tyrosinase," in Enzymes in Polymer Synthesis (Gross et al., eds.), American Chemical Society, pp. 188-198 (1998), the disclosure of which is incorporated herein by reference in its entirety.

Although there have been some successes in enzyme-modification of polymers, these biotechnological approaches suffer from a number of practical disadvantages. Many such reactions are too slow to be commercially practical, are not readily controlled, employ prohibitively expensive reagents, or are limited by the surface-orientated nature of heterogeneous phase reactions as described above.

It is thus desirable to develop new chitosan derivatives which have important functional properties such as broad water-solubility. It is further desirable to develop new ways to produce such polymers without employing hazardous chemicals or generating potentially environmentally hazardous waste streams. It is particularly desirable to develop ways to modify naturally-occurring polymers to confer desired functional properties in simple, versatile, and environmentally clean ways.

3. SUMMARY OF THE INVENTION

The present invention relates to methods of producing modified chitosan oligomers and polymers, and modified chitosan oligomers and polymers produced therefrom. In one aspect, the invention relates to a method which comprises reacting an enzyme with a phenolic compound in the presence of a chitosan polymer or oligomer, wherein the reaction is carried out in a solution at a pH sufficient to solubilize the chitosan starting material. The phenolic compound can be any compound having a phenolic moiety, and can include phenols or substituted phenols, as well as peptides, proteins and natural or synthetic polymers having one or more phenolic substituents. The chitosan starting material can be a chitosan polymer of low, medium or high molecular weight, a chitosan oligomer, a chitosan monomer (i.e., glucosamine), or any of the above chitosan materials which have been modified or derivatized by the present processes or other processes. The enzyme can be any enzyme that uses molecular oxygen as the oxidizing agent and converts phenols to quinones, such as a tyrosinase, a phenol oxidase or a polyphenol oxidase.

In another aspect, the invention relates to a method of producing a modified chitosan polymer or oligomer that is soluble in aqueous alkaline solution, which comprises reacting an enzyme with a phenolic compound in the presence of a chitosan polymer or oligomer, wherein the reaction is carried out in an aqueous solution at a pH sufficient to solubilize the chitosan polymer.

In yet another aspect, the invention relates to a method of producing a modified chitosan polymer or oligomer having a high viscosity, which comprises reacting an enzyme with a phenolic compound in the presence of a chitosan polymer or oligomer, wherein the reaction is carried out in an aqueous solution at a pH sufficient to solubilize the chitosan polymer or oligomer.

In another aspect, the invention relates to a method of producing a modified chitosan polymer or oligomer, which comprises:

(a) solubilizing a chitosan polymer or oligomer in aqueous solution;

(b) reacting an enzyme with a phenolic compound in the presence of the chitosan polymer or oligomer to produce a modified chitosan polymer or oligomer;

(c) solubilizing the modified chitosan polymer or oligomer in aqueous solution; and (d) reacting an enzyme with a phenolic compound in the presence of the modified chitosan polymer or oligomer to produce a further modified chitosan polymer or oligomer.

In this aspect, steps (c) and (d) can be repeated to further modify the modified chitosan polymer or oligomer.

In another aspect, the invention includes modified chitosan polymers and oligomers produced by the presently disclosed processes.

4. BRIEF DESCRIPTION OF THE DRAWINGS

5. DETAILED DESCRIPTION OF THE INVENTION

Figure 1:
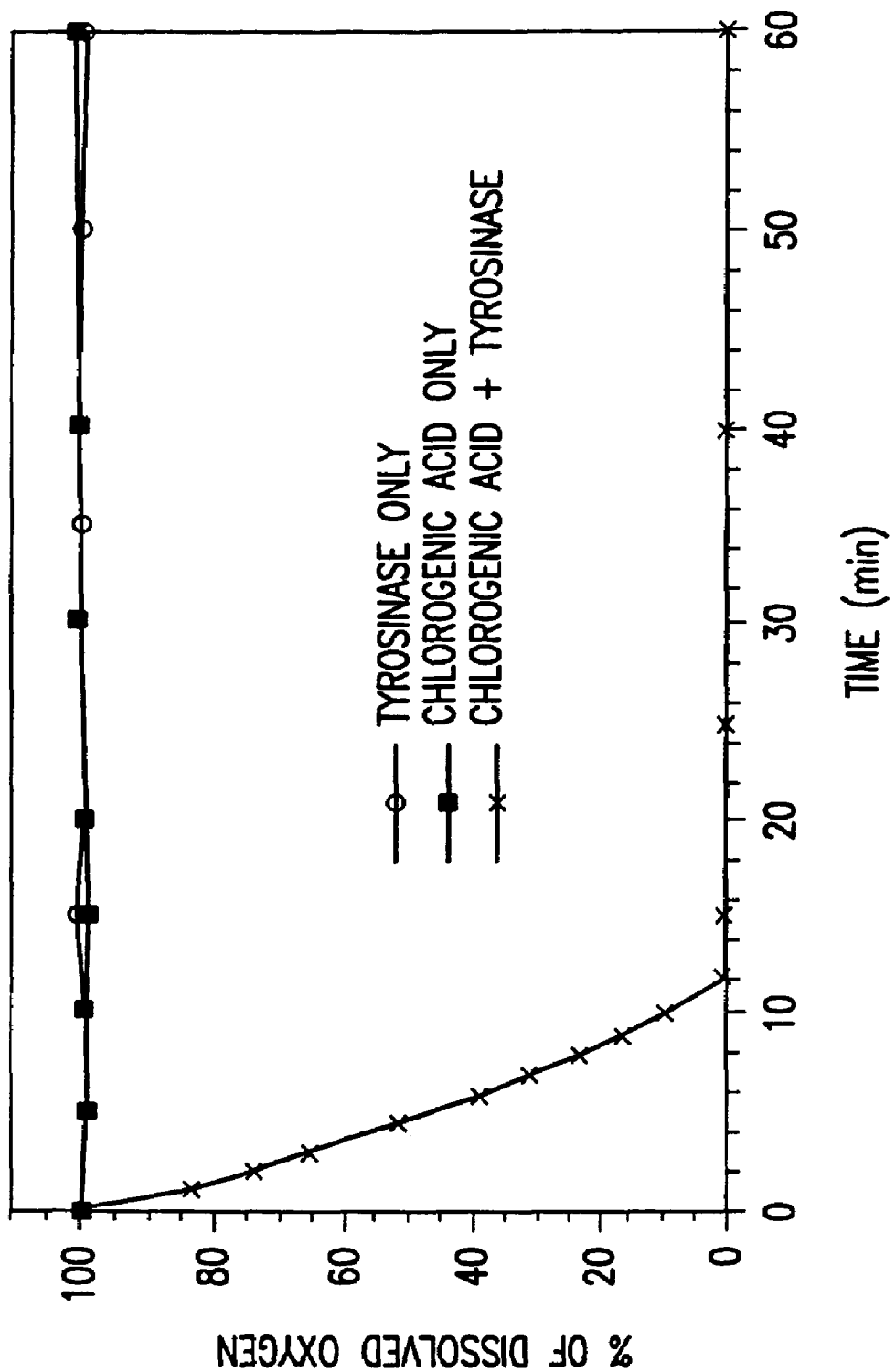
FIG. 1 shows the dissolved oxygen content as a function of time during the progress of an enzyme-catalyzed chitosan modification reaction.

The present invention provides a method for preparing chitosan polymers or oligomers having useful functional properties, including solubility in aqueous alkaline solution, high viscosity, biological activity or enhanced biological stability or activity, and the like. These modified chitosan polymers and oligomers are prepared by a homogeneous phase process, wherein an enzyme is reacted with a phenolic compound in the presence of chitosan to form a modified chitosan polymer or oligomer. The present method allows the synthesis of new polymers or oligomers based on the naturally-occurring polymer chitosan, without the need for organic solvents or highly reactive reagents. Moreover, since the reaction takes place with the chitosan in solution with the enzyme and the phenolic compound (i.e., homogeneous phase), the present method avoids the problems with reaction rate and uniformity associated with heterogenous phase reactions in which an insoluble chitosan (as a powder, film or gel, for example) is used. The invention also provides novel chitosan polymers or oligomers produced by the presently disclosed methods.

5.1. Enzyme-Catalyzed Modification of Chitosan

In one embodiment, the present invention relates to a process for modifying a chitosan polymer or oligomer, using an enzyme-catalyzed reaction. The process is carried out in solution and at a pH sufficient to solubilize the chitosan polymer, under homogeneous phase conditions.

The term "chitosan polymer or oligomer" as used herein includes any chitosan, such chitosan isolated from natural sources, or commercially-available chitosan, such as from various suppliers (e.g., Aldrich, Sigma), without regard to the particular average molecular weight of the polymer; i.e., oligomers and "low" (typically above about 10,000 g/mol), "medium" (typically about 100,000 to 300,000 g/mol), or "high" (typically above about 300,000 g/mol) molecular weight chitosan polymers can be used. As is well known in the art, chitosan is conventionally produced by deacetylation of chitin, and various grades of chitosan having different average molecular weight and different extents of deacetylation can be prepared. Thus, the term "chitosan polymer or oligomer" includes chitosan with complete or nearly complete deacetylation (e.g., 90-100%), or equally chitosan with less complete deacetylation. The term "chitosan polymer or oligomer" also includes various derivatives of chitosan having the necessary solubility in the reaction solution and having at least a portion of the amino functional groups available for reaction. In particular, "chitosan polymer or oligomer" includes chitosan modified by the process described herein; i.e., the presently described process can be used iteratively, with the modified chitosan polymer or oligomer produced as a product in one iteration used as the reactant "chitosan polymer or oligomer" in a subsequent iteration. The term "chitosan polymer or oligomer" also includes chitosan modified or derivatized by other processes. Thus, the term "chitosan polymer or oligomer" includes both modified and unmodified chitosan.

In order to modify chitosan in the process of the present invention, the chitosan polymer or oligomer must be solubilized, so that the subsequent reactions take place under homogeneous (solution) phase conditions. When the chitosan polymer is unmodified chitosan of medium or high molecular weight, it can be mixed in solution at an acidic pH until most of the chitosan is dissolved. The pH can be less than about 6.5. Preferably, chitosan is stirred for several hours or overnight in a solution of pH about 2-3, and any undissolved material remaining is removed by filtration and/or centrifugation to yield a homogeneous chitosan solution. When the chitosan polymer is a modified chitosan or a chitosan oligomer, the pH of the solution in which the chitosan polymer is solubilized can be adjusted as necessary to achieve solubilization. The chitosan polymer can also be a mixture of chitosan polymers of different molecular weights, a mixture of different modified chitosans, or a mixture of modified and unmodified chitosan, provided that the mixture can be solubilized.

The solution in which the chitosan is solubilized can be an aqueous solution, including mixtures of alcohol and water, or an alcohol solution, depending upon the solubility characteristics of the chitosan. The solution can include any salts, buffers, or other components which do not react with chitosan. The solution can also be a mixture of one or more phenolic compounds with alcohol or water. For medium and high molecular weight chitosan polymers, the solution is typically an aqueous solution.

Once the chitosan polymer or oligomer is solubilized, it can be diluted as desired to give a convenient working concentration. It is convenient to prepare a chitosan solution of about 1-3% (by weight), and dilute the solution somewhat to obtain a working solution of about 0.1 to about 0.5%. Chitosan solutions of greater or lesser concentration can be used, as desired. One measure of the chitosan concentration is the equivalent molar concentration of amino groups. Since each chitosan monomer has one amino group, assuming complete deacetylation, the equivalent concentration of amino groups in solution can be calculated. Using this measure, an equivalent amino group concentration of about 10 mM corresponds to a 0.16% chitosan solution. For illustrative purposes, we have used aqueous chitosan solutions of about 0.1 to 0.6% (5-30 mM).

A reaction solution is provided with the chitosan polymer or oligomer, the phenolic compound, and the enzyme. The order of mixing can be any convenient order; i.e., the phenolic compound, the chitosan, and the enzyme can be combined in any order, or the chitosan can be solubilized in a solution which already contains the phenolic compound and/or the tyrosinase. Phenolic compounds suitable for use in the present invention are described in detail below. Mixtures of phenolic compounds are also suitable for the present methods. The amount of the phenolic compound used can be any amount sufficient to consume all or part of the amino moieties of the chitosan polymer or oligomer. As a specific illustration, for non-polymeric phenolic compounds, the amount is typically about 1-500%, where the percentage represents the mole percentage of phenolic compound, based on the total number of moles of amino groups present in the chitosan polymer. For example, if the equivalent amino group concentration is 10 mM, a 50% concentration of the phenolic compound would be 5 mM, and the phenolic compound can be added to give a concentration anywhere in the range of about 0.1 to about 50 mM (1 to 500% of 10 mM). Preferably, in such case the phenolic compound is present in an amount of about 5 to about 80%, more preferably about 30-80%, and most preferably about 60%, based on the number of chitosan amino groups.

As discussed above, the amino groups of chitosan can be protonated and deprotonated, depending on the pH of the solution. At low pH, the amino groups are protonated, and the chitosan is water-soluble. Thus, it is convenient to solubilize unmodified chitosan in acidic solution. However, at low pH, the protonated amino groups are unreactive toward electrophilic reagents such as quinones. At a more basic pH, the amino groups are neutral and nucleophilic; however, the non-charged chitosan is poorly soluble in water. Thus, an important aspect of the present invention is the careful adjustment of solution pH to a pH at which enough of the amino groups are protonated to render the chitosan water-soluble, but enough of the amino groups are neutral to react with electrophilic quinones. Thus, the pH at which the chitosan is conveniently solubilized need not be the same as the pH at which the reaction is run. Further, a pH must be chosen such that the enzyme remains active and stable. The present inventors have found that this pH "balance" between solubility and reactivity for unmodified chitosan occurs at a pH close to the $pK_a$ of the unmodified chitosan polymer, 6.3. In this case, the solution pH can be about 5.5 to about 6.5, preferably about 5.8 to about 6.3. Modified chitosan polymers may have a different solubility property which can be readily determined, and the appropriate solution pH is adjusted to permit solubility, neutral amino groups, and enzyme activity.

For lower molecular weight chitosan polymers and oligomers which are soluble over a broader pH range, the pH must be selected to be consistent with neutral amino groups and enzyme activity. Thus, for any of the chitosan polymers or oligomers, including modified chitosan polymers or oligomers, the pH of the solution is bounded by the following factors which can readily be determined by the skilled artisan:

(1) the chosen enzyme must be active at the desired pH;

(2) at least a portion of the chitosan amino groups must be deprotonated (neutral); and (3) the chitosan must be soluble at the desired pH in order to carry out the reaction under homogeneous phase conditions.

The pH of the solution of the chitosan polymer can be adjusted if necessary to the desired value for carrying out the enzyme-catalyzed reaction by addition of a non-reactive base, preferably a non-reactive inorganic base such as sodium hydroxide, or a non-reactive acid such as hydrochloric or acetic acid. It is convenient to adjust the solution pH after the phenolic compound and the chitosan polymer or oligomer are together in solution, since the phenolic compound may have an effect on the solution pH.

The specific enzymes which are suitable for use in the processes of the present invention are described in detail below. Mixtures of suitable enzymes are also within the scope of the invention.

Once the solubilized chitosan polymer or oligomer, the phenolic compound and the enzyme are present in solution, and the pH adjusted to a desired value, the reaction commences. The specific activity of the enzyme used will determine how much of the enzyme should be added. As an illustration, for a mushroom tyrosinase enzyme, a convenient level is from about 10 to about 200 U/mL, preferably about 20 to 100 U/mL, and most preferably about 60 U/mL. Higher amounts of the enzyme may result in depletion of the phenolic compound or of molecular oxygen in the solution. The reaction is then allowed to proceed, conveniently with stirring overnight.

The resultant reaction product is a chitosan polymer or oligomer which has been modified by reaction in the presence of the enzyme and the phenolic compound. The term "modified" as used herein means that the chitosan has chemically reacted with one or more species in solution. Without being bound by any particular theory, it is believed that the enzyme converts the phenolic compound to a reactive quinone species, and the chitosan polymer or oligomer then reacts to covalently bond with the quinone or species derived from the quinone. More than one type of chitosan-quinone interaction is possible; for example, it has been suggested that the quinone-chitosan reaction takes place via a Schiff base intermediate or product, or a Michael's adduct intermediate or product. Further, depending on the specific chemical structure and reactivity of the phenolic compound and quinone intermediate, the chitosan may undergo additional conformational changes upon reaction with the quinone, or further chemical reaction with the species in solution. For example, when tyrosinase is reacted with certain phenolic compounds such as p-cresol, catechol and dopamine, the resultant modified chitosan polymer forms a highly viscous hydrogel, presumably due to chemical crosslinking and/or physical entanglement of the chitosan polymer chains. Thus, a "modified" chitosan polymer includes chitosan polymers with a quinone or quinone-derived species covalently attached (i.e., simple derivatives), as well chitosan polymers which, having reacted with the enzyme-generated quinone, subsequently undergo further chemical reaction or physical changes.

The modified chitosan polymers and oligomers produced by the present processes can be isolated if desired using conventional techniques such as are well-known in the art. Modified chitosan polymers having base solubility, and insolubility at neutral pH, such as those described in the Examples herein, can be isolated if desired by adjusting the solution pH so that the modified chitosan precipitates. Preferably, the aqueous reaction solution is first brought to a pH above about 8, more preferably about 13-14, by addition of a base such as sodium hydroxide. The solution can be stirred for about 24 hours to completely dissolve the modified chitosan. At high pH, unmodified chitosan is insoluble, whereas the modified chitosan polymers are soluble. Thus, any precipitate (unmodified chitosan) can be separated by centrifugation or filtration and discarded. The supernatant solution, containing modified chitosan, can then be neutralized by addition of an acid such as HCl to a pH of about 7, where the modified chitosan polymer will precipitate. The precipitate is collected by filtration and/or centrifugation, and washed several times with deionized water.

The modified chitosan can be further treated as desired. For example, the modified chitosan can be subjected to other modification procedures, such as further enzyme modification, or conventional chemical modification. In the latter case, the initial enzymatic modification can be used to create a modified chitosan with the desired physical or chemical properties (e.g., appropriate solubility or chemical functionality). As noted above, it is also possible to subject chitosan derivatives which have been modified through alternative techniques (such as conventional chemical modification) to the present enzymatic treatment.

In another embodiment, the present invention relates to an iterative method of producing a modified chitosan polymer or oligomer in which the steps of solubilizing the chitosan polymer or oligomer and modifying it with an enzyme-generated reactive quinone species are repeated as many times as desired to obtain a modified chitosan polymer or oligomer having the desired functional properties. In this aspect, the method comprises (a) solubilizing a chitosan polymer or oligomer;
(b) reacting an enzyme with a phenolic compound in the presence of the chitosan polymer or oligomer to produce a modified chitosan polymer or oligomer;
(c) solubilizing the modified chitosan polymer or oligomer; and
(d) reacting an enzyme with the phenolic compound in the presence of the modified chitosan polymer or oligomer to produce a further modified chitosan polymer or oligomer.

The steps (c) and (d) can be repeated in an iterative process, with the reaction product from (d) in each iteration becoming the modified chitosan reagent used in step (c) of the subsequent iteration. Between steps (b) and (c), the modified chitosan can be isolated, purified, or characterized if desired. Alternatively, the modified chitosan produced in (b) can remain in solution and be subsequently further modified without any intermediate isolation or purification processes. In such case, the "solubilizing" step (c) can be carried out simply by adjusting the solution pH, as desired, to the appropriate value to optimize the reactivity-solubility-enzyme activity balance, as described above. Similarly, if steps (c) and (d) are repeated, the product of (d) in one iteration can be isolated, purified or characterized, if desired, or can simply be maintained in solution and the process continued in step (c). Suitable enzymes are described below.

The reaction in step (b) can be carried out at a desired pH as described above. The pH of the reaction solution in step (d) similarly depends on the solubility characteristics of the modified chitosan, the need to provide neutral amino groups, and the enzyme activity.

In another aspect, the present invention relates to modified chitosan polymers or oligomers produced by the processes of the present invention. These modified chitosan polymers or oligomers can possess surprising and unexpected functional properties and/or physical characteristics. Without wishing to be bound by theory, it is believed that when conventional heterogeneous phase processes for chitosan modification are used, using for example chitosan films or gels, modification only occurs on the outer chitosan surface, with the regions less accessible to the solution phase remaining largely unmodified. In contrast, modification by the homogeneous phase process of the present invention is believed to result in more uniform modification, enabling the production of modified chitosan polymers or oligomers having unusual and surprising characteristics.

For example, when phenolic compounds such as p-cresol, caffeic acid and chlorogenic acid are used in the present invention, the resultant modified chitosan polymers surprisingly and advantageously possess useful solubility characteristics such as solubility in aqueous alkaline solution and aqueous acidic solution, with a "window" of insolubility at intermediate, near-neutral pH.

As a further example, when phenolic compounds such as p-cresol, catechol and dopamine are used in the present invention, the resultant modified chitosan polymers surprisingly and advantageously possess useful rheological characteristics such as the ability to form highly viscous hydrogels. Specific examples of modified chitosan polymers having these unexpected functional and physical properties are given in the Examples section below.

5.1.1 Phenolic Compounds

The phenolic compound can be any compound which can be brought into solution at the desired pH, and reacts with an enzyme as described below. The solution can be an aqueous solution, an alcohol, or a water/alcohol mixture, as described above. Other solvents or solvent mixtures, including organic solvents may also be used; suitable solvents are those which are capable of dissolving the reagents to provide homogeneous phase conditions, and which permit reaction by the enzyme. The skilled artisan can readily determine the solubility of a phenolic compound in solution of a particular composition and pH. Mixtures of phenolic compounds can also be used. Phenolic compounds which react with the enzymes described herein are well-known in the art, and are disclosed, for example, in U.S. Pat. No. 5,340,483. Moreover, the enzymes described below, such as tyrosinases, phenol oxidases and polyphenol oxidases, are known to react with a broad range of substrates having phenolic moieties, including polymers, peptides and proteins. Thus, phenolic compounds suitable for use in the present invention include, but are not limited to, phenols and substituted phenols; natural or synthetic polymers or oligomers having at least one phenolic moiety; peptides having at least one phenolic moiety; and proteins having at least one phenolic moiety.

As a non-limiting example of phenols and substituted phenols suitable for the present invention are compounds having the formula:

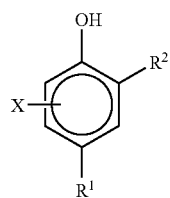

(III)

wherein $R^1$ is any moiety that is not highly reactive to chitosan, and can be, for example, hydrogen, hydroxyl, alkyl or substituted alkyl, alkenyl or substituted alkenyl, alkynyl, cycloalkyl or substituted cycloalkyl, cycloalkenyl or substituted cycloalkenyl, aryl or substituted aryl, amino or substituted amino, carboxylic acid or carboxylic acid esters, aldehyde or ketone groups, or multi-functional substituents having two or more of the above recited functional groups;

$R^2$ is H or OH; and

X is one or more additional substituents that can be halogen, hydroxy, alkyl or substituted alkyl, alkenyl or substituted alkenyl, cycloalkyl or substituted cycloalkyl, cycloalkenyl or substituted cycloalkenyl, aryl or substituted aryl, amino or substituted amino, carboxylic acid or carboxylic acid esters, aldehyde or ketone groups, multi-functional substituents having two or more of the above recited functional groups, or two adjacent substituents which are joined to form a ring. Such compounds are available commercially, or can be synthesized by methods known in the art.

For example, when X is H, $R^1$ can be H, in which case the phenolic compound is phenol ($R^2$=H) or catechol ($R^2$=OH). $R^1$ can be a small alkyl group such as methyl, in which case the phenolic compound is p-cresol ($R^2$=H) or methylcatechol ($R^2$=OH). $R^1$ can also be a substituted alkyl group, such as ethylamine (—$CH_2CH_2NH_2$), in which case the phenolic compound is tyramine (4-(2-aminoethyl)phenol) ($R^2$=H) or dopamine (3-hydroxytyramine) ($R^2$=OH).

$R^1$ can also be a multifunctional substituent. For example, X can be H and $R^1$ can be a vinylacetic acid group, —CH=CHC(O)OH, in which case the phenolic compound is 4-hydroxycinnamic acid ($R^2$=H) or caffeic acid (3,4-dihydroxycinnamic acid) ($R^2$=OH), or an ester thereof.

As further examples, X can be a halogen such as chloride, in which case the phenolic compound can be a chlorophenol, with $R^1$ and $R^2$ being chosen as described above. X can also be a hydroxy group; for example, when X is OH in the 3 position and $R^1$ and $R^2$ are H, the phenolic compound is resorcinol. When X is two adjacent substituents forming a ring, the phenolic compound can be, for example, naphthol.

Thus, specific, non-limiting examples of phenolic compounds suitable for use in the present invention include phenol, 2-chlorophenol, 2,2'-dihydroxybiphenyl, 8-hydroxyquinoline, 3-amino-phenol, o-cresol, m-cresol, p-cresol, 2,3-dimethylphenol, 2-methoxyphenol, resorcinol, 1-nitrosonaphthol, hydroquinone, 4-chlorophenol, 4,4'-dihydroxybiphenyl, 2-aminophenol, 3-methoxyphenol, 1-naphthol, 4-phenylphenol, p-hydroxyphenoxyacetic acid, 5-methylresorcinol, tert-butylcatechol, catechol, methylcatechol, tyramine, dopamine, caffeic acid, hydroxycinnamic acid and chlorogenic acid, to name but a few.

The phenolic compound can also be a polymer or oligomer having at least one phenolic moiety, or a peptide or a protein having at least one phenolic moiety or tyrosine residue. Such species are well known to one skilled in the art.

The invention also relates to modified chitosan polymers produced by the presently disclosed processes. When a modified chitosan polymer having solubility in aqueous alkaline solution is desired, the phenolic compound can be, for example, p-cresol, chlorogenic acid or caffeic acid. When a modified chitosan polymer having high viscosity is desired, the phenolic compound can be, for example, p-cresol, catechol or dopamine.

5.1.2 Enzymes

Enzymes suitable for use in the present invention are well known in the art, and include enzymes having the properties of (1) using molecular oxygen as the oxidant; and (2) reacting with phenolic moieties to generate species which react with chitosan. Without wishing to be bound by theory, it is believed that such enzymes convert phenols to quinones, which then react with the neutral amino groups on chitosan. Such enzymes are readily available commercially, and are ubiquitous in natural sources. Examples of such enzymes include, but are not limited to, tyrosinases, phenol oxidases, and polyphenol oxidases. As discussed above, the presently disclosed processes can be carried out at a pH chosen to accommodate neutral amino groups and chitosan solubility, as well as enzyme activity. Enzymes which meet the reactivity criteria above are readily found in nature, and when a particular pH is desired for reactivity and solubility reasons, one skilled in the art can readily identify and find an appropriate enzyme which has the required reactivity at the desired pH. For illustrative purposes, the Examples herein use a tyrosinase, specifically a mushroom tyrosinase available commercially (Sigma) However, other suitable enzymes may also be used, as described herein.

5.2. Use of Modified Chitosan

The modified chitosan polymers and oligomers of the present invention can be used in a variety of applications, depending on their functional properties. For example, base-soluble chitosan polymers can be used in any application in which such solubility is advantageous. Further, since the modified chitosan polymers can be prepared having a low degree of substitution, as shown in the Examples below, base-soluble modified chitosan polymers of the present invention still contain many unmodified amino sites. Thus, base-soluble modified chitosan polymers can be reacted and derivatized in alkaline solution, where the reactivity is greater than for unmodified chitosan polymers, thus enabling a wide variety of chitosan derivatives to be prepared that were impossible or impractical to prepare under more acidic, less reactive conditions. Such further reaction and derivatization can be carried out by the processes of the present invention, or by other methods of chitosan modification, including chemical reaction. Still further, such additional modifications can utilize the reactivity of moieties attached to the chitosan. For example, when chitosan is modified according to the present invention with dopamine as the phenolic compound, further derivatization can make use of the amino functionality on the dopamine moiety. It will be apparent to one skilled in the art that a wide variety of functionalities can be present on the attached moiety, depending upon the phenolic compound used in the reaction, and the chemical, physical and biological properties of such moieties can be utilized as desired.

Moreover, the base soluble modified chitosan polymers can be further modified by the methods of the invention to create modified chitosan polymers with still more surprising and useful functional properties. As but one example, modified base-soluble chitosan polymers can be further modified by reaction in the presence of an enzyme and a phenolic compound, wherein the phenolic compound is chosen to impart a high viscosity to the resultant further modified chitosan polymer. Thus, the high-viscosity gels described herein can be formed in alkaline solution, using base-soluble modified chitosan as the starting material.

The high-viscosity modified chitosan polymers and oligomers of the present invention can similarly be used wherever their functional properties are desired. For example, since these polymers are based on naturally occurring chitosan, or modified chitosan polymers, they can be used in environments where the use of a synthetic polymer is environmentally problematic. In but one example, the processes and compounds of the present invention can be used in applications such as profile modification, in which porous geological structures (permeable zones) can be filled or sealed with a high-viscosity modified chitosan gel. In this example, an aqueous solution of a chitosan polymer and a phenolic compound can be provided to a more permeable zone, for example by pumping. An aqueous tyrosinase solution can then also be provided to the more permeable zone, such that the tyrosinase and the phenolic compound react in the presence of the chitosan polymer to form a high-viscosity gel, effectively sealing the permeable zone. In alkaline zones in which a chitosan polymer solution would precipitate the polymer, a modified base-soluble chitosan polymer of the present solution can be used. Such a gel is particularly useful in profile modification, since it is desired to seal permeable zones, while the use of other polymer systems is impractical or environmentally harmful. Since chitosan can be degraded by naturally occurring enzymes well-known to the skilled artisan, the high-viscosity chitosan-based gel can be removed enzymatically, if desired, without harmful environmental consequences. Many other such useful applications of the modified chitosan polymers of the present invention will be apparent to those skilled in the art, and are within the scope of the present invention.

Certain embodiments of the invention are illustrated, and not limited, by the following working examples.

6. EXAMPLES

In the following Examples, unless otherwise indicated, the materials, methods and conditions were as follows:

Materials

All of the reagents and solvents used are available commercially from various suppliers. Chitosan and chlorogenic acid were obtained from Sigma Chemical Co. The chitosan used in these examples had an average molecular weight of about 300,000 g/mol, and a degree of deacetylation of about 90%, as determined by NMR analysis. For the NMR studies, $D_2O$ was obtained from Cambridge Isotope Laboratories. The tyrosinase used was mushroom tyrosinase, obtained from Sigma, and was reported by the supplier to have a specific activity of 3,000 U/mg. All other chemicals used were obtained from Fisher Scientific.

Methods

Aqueous solutions of chitosan were prepared by suspending 1.6 g of chitosan in 100 mL of water (deionized), and acidifying the solution to a pH of about 2 by slowly adding 2 M HCl. The solution was mixed overnight, and any undissolved material was then removed from the solution by vacuum filtration. The resulting solution was a viscous aqueous solution of 1.6% (w/v) chitosan.

For homogeneous phase reactions, the 1.6% chitosan solution was diluted by a factor of ten to form a 0.16% solution. At this concentration of 0.16%, the solution contained an equivalent amino group concentration of about 10 mM, assuming that the deacetylation of chitin to chitosan was 100%. Analysis by NMR showed a somewhat lower extent of deacetylation (about 90%), so that the actual equivalent amino group concentration was slightly lower than the calculated 10 mM level.

For heterogeneous phase comparison reactions, insoluble chitosan gels were prepared by immersing petri dishes (3.5 cm) containing the 1.6% chitosan solution in 0.25 M NaOH for about 4 to 5 hours. The resulting gels were then removed from the dishes and thoroughly washed with deionized water.

6.1. Example 1

Enzymatic Activity of Tyrosinase Under Acidic Conditions

The reactivity of tyrosinase under mildly acidic conditions was studied to verify that the enzyme remains active in acidic solution. The progress of the reaction was measured by monitoring the consumption of dissolved oxygen, using the method described in Mayer et al., "Assay of catechol oxidase: A critical comparison of methods," *Phytochem.*, 5:783-789 (1966). The dissolved oxygen probe used in these measurements was obtained from Microelectrodes, Londonderry, N.H. Chlorogenic acid (6 mM) was added to a 0.16% chitosan solution, and the pH was adjusted to about 5.8 to 6.0. Tyrosinase (60 U/mL) was added, the reaction vessel sealed, and the dissolved oxygen content measured as a function of time. Two control solutions were prepared and monitored in the same manner, one containing only tyrosinase and chitosan (no phenolic compound), and one containing only chlorogenic acid and chitosan (no enzyme). The results of these measurements are shown in FIG. 1, with the two control solutions labeled "tyrosinase only" and "chlorogenic acid only," respectively. As the Figure shows, in both of the control solutions the dissolved oxygen content remained unchanged throughout the measurement period. In the solution containing both tyrosinase and chlorogenic acid, however, the oxygen level dropped rapidly in the first few minutes, reaching essentially zero after about 10 to 12 minutes. This measurement indicates that tyrosinase remained active in this pH range, catalyzing the oxidation of the phenolic substrate to the corresponding quinone and thereby depleting the solution of dissolved oxygen.

6.2. Example 2

Preparation and Characterization of Base-Soluble Modified Chitosan Polymers A chitosan polymer modified with chlorogenic acid was prepared. A 0.16% chitosan solution was incubated with chlorogenic acid (6 mM) and tyrosinase. The resulting modified chitosan polymer is designated as "60%", since the reacting solution contained a molar ratio of chlorogenic acid to chitosan amino groups of 0.6 (i.e., the equivalent amino group concentration was 10 mM). The reaction was carried out in a 150 mL beaker with a total of about 25 mL of solution with constant stirring, and the beaker was left open to air in order to minimize any problems associated with oxygen depletion in the solution. A dissolved oxygen probe was used to monitor the reaction, and measurements indicated that the amount of dissolved oxygen remained at about 70% relative to the air saturation value.

As the reaction proceeded, the initially colorless solution turned brown, and a dark precipitate formed. The reaction was allowed to run overnight before collection and analysis of the modified chitosan polymer.

The modified chitosan was characterized as follows. The solution pH was adjusted using aqueous sodium hydroxide, to a value of about 13-14, and the solution mixed for 24 hours. The dark precipitate was observed to dissolve. In order to ensure that any unreacted chlorogenic acid was removed, the solution pH was readjusted to a value of about 7, where the precipitate again appeared. The precipitate was collected by centrifugation and washed twice with deionized water. A control experiment was also performed to ensure that the observed chitosan modifications were in fact caused by the enzyme-catalyzed reaction and not by the subsequent base treatments. Solutions containing chitosan and chlorogenic acid were prepared and subjected to the process as described above, but no tyrosinase was added. Unlike the tyrosinase-containing solution, the control solution contained insoluble precipitates which did not dissolve after 24 hours of the base treatment. Neutralization of the control solution resulted in a precipitate, but the collected precipitate (centrifuged) was white, as is chitosan, and not brown, as is the chlorogenic acid modified chitosan.

The solubility characteristics of chitosan and the chlorogenic acid modified chitosan were compared. Under acidic conditions (pH of 1), both the chitosan and the modified chitosan were observed to be soluble. When the pH was increased to about 9, the chitosan solution formed a gel, whereas the modified chitosan remained in solution. Finally, when the pH was adjusted to about 7, the chitosan remained in an insoluble gel form, and the modified chitosan precipitated out. After the modified chitosan was allowed to settle for about 30 minutes, the supernatant solution was observed to be clear. Thus, chitosan modified by the present process using chlorogenic acid as the phenolic compound was observed to be soluble in acidic and basic solution, but insoluble in neutral solution.

6.3. Example 3

Preparation And Characterization of "Twice Reacted" Base-Soluble Modified Chitosan Polymers A modified chitosan polymer was prepared according to Example 2. The collected and washed modified chitosan polymer was redissolved at high pH, then the pH was adjusted to about 8 by addition of hydrochloric acid. The solubilized modified chitosan was then incubated overnight with tyrosinase and 6 mM chlorogenic acid, as in Example 2. After reaction, the "twice reacted" or further modified chitosan polymer was collected and washed. It was observed to have a dark brown color, qualitatively darker than the starting material, and a stronger 340 nm absorbance.

6.4. Example 4

Effect of Phenolic Compound Concentration on Base-Soluble Modified Chitosan Polymers The experiment of Example 2 was repeated, but the amount of chlorogenic acid was varied to examine the effect of phenolic compound concentration on the properties of the resultant modified chitosan polymer. Three different chlorogenic acid concentrations were used: 0.5 mM, 3.0 mM, and 6.0 mM, corresponding to 5, 30 and 60% respectively of the chitosan amino groups. Solutions of the resultant modified chitosan polymers (collected and washed) at various pH levels were prepared and characterized by UV absorbance, using a UV spectrophotometer at a wavelength of 340 nm. For convenience, each solution was initially prepared either at low pH (about 1) or high pH (about 14). A sample was taken from the solution, centrifuged to separate any insoluble material, and the absorbance of the supernatant solution measured. Then, the pH of the starting solution was adjusted approximately to the next integral value incrementally (e.g., the pH 1 solution was brought to pH 2, then 3, etc.), with the sampling and measuring procedure repeated at each pH value.

Figure 2:
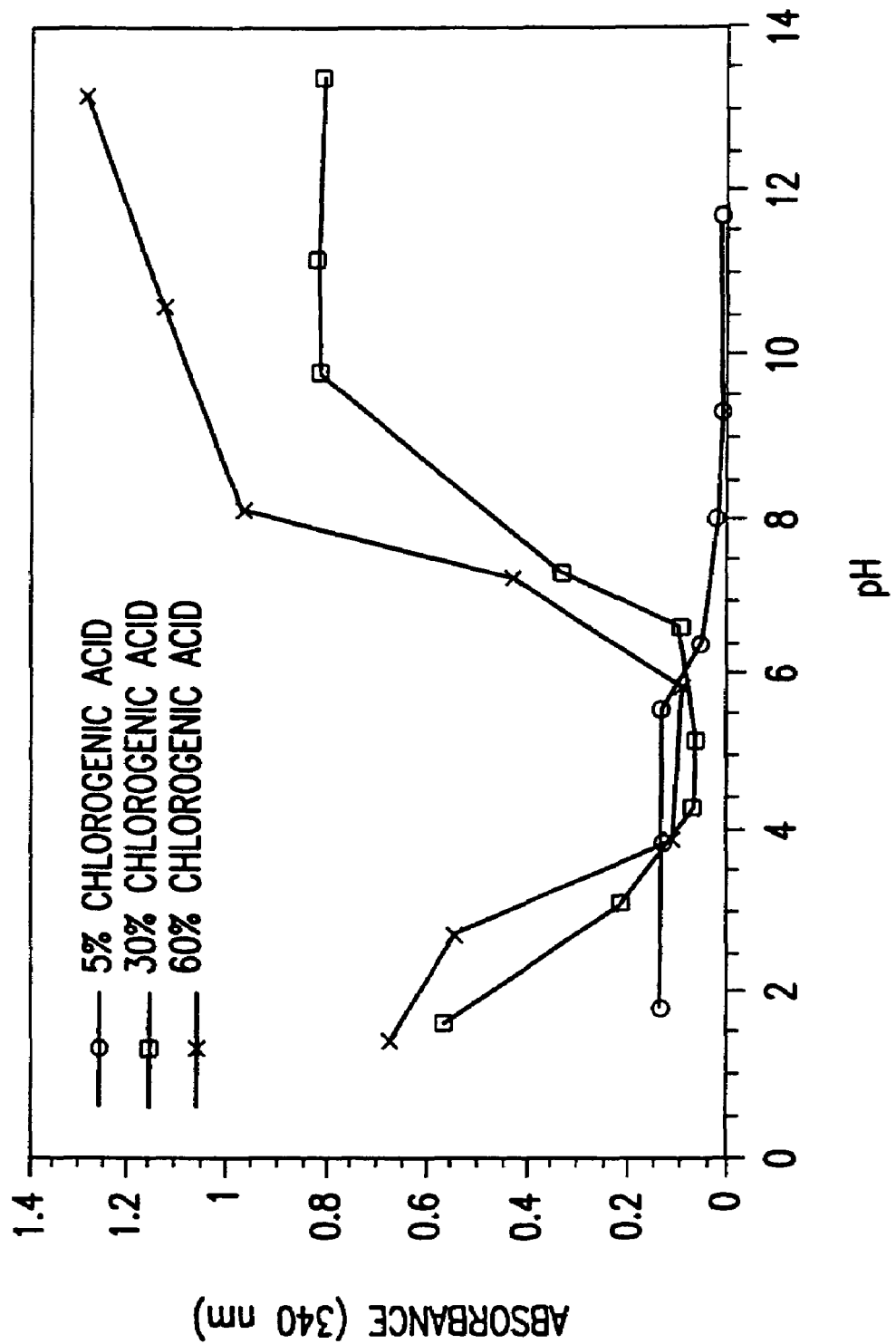
FIG. 2 shows the UV absorbance of modified chitosan polymers in solutions of different pH.

The UV measurements are shown in FIG. 2. Unmodified chitosan, not shown in the figure, does not absorb at 340 nm. The 5% sample had a light brown color and showed weak absorbance at low pH, indicating the presence of modified chitosan. The 30% sample was considerably darker in color, and showed absorbance at both acidic and alkaline pH, with a drop in absorbance at neutral pH corresponding to formation of a brown precipitate. The 60% sample was still darker, and showed a UV absorbance and pH-solubility profile similar to those of the 30% sample.

6.5. Example 5

NMR Analysis of Base-Soluble Modified Chitosan Polymers

The base soluble modified chitosan polymer of Example 2 was analyzed by proton NMR to confirm that the base-soluble precipitate was in fact a chitosan polymer, rather than, for example, a compound formed from a quinone-quinone side reaction. Samples were prepared using chitosan and the modified chitosan of Example 2. The heteroatom hydrogens were exchanged with deuterium by adding $D_2O$ to the sample and evaporating away the solvent several times. Spectra were collected using either a 300 MHz or 500 MHz General Electric NMR. At low pH, the spectra were collected at elevated temperature (80° C.) to shift the HOD peak from 4.8 to 4.2 ppm in order to avoid interference from the anomeric proton. Spectra for high pH solutions were taken at room temperature.

Figure 3A:
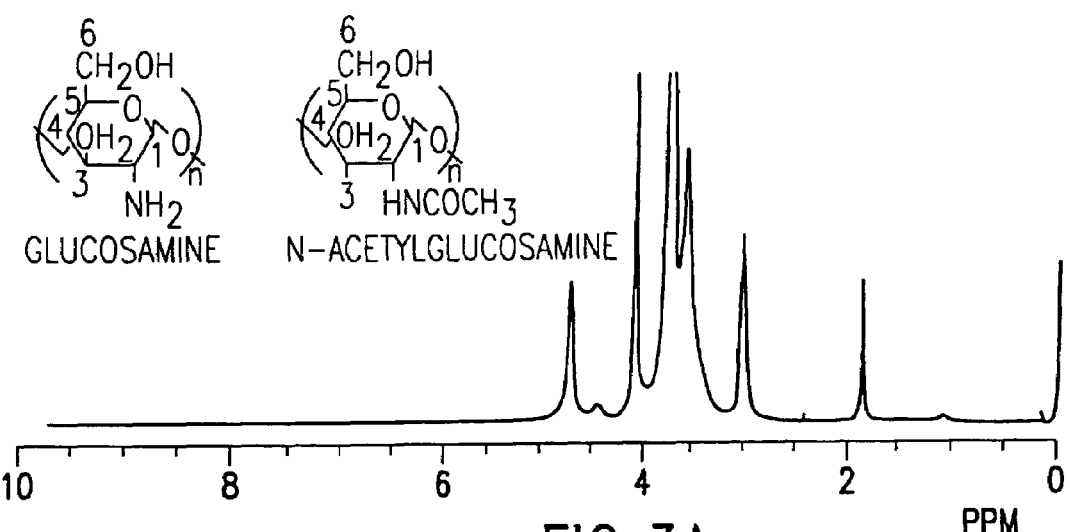
FIGS. 3(A-C) show the $^1$NMR spectra of chitosan (Sigma) and modified chitosan polymers of the present invention.
Figure 3B:
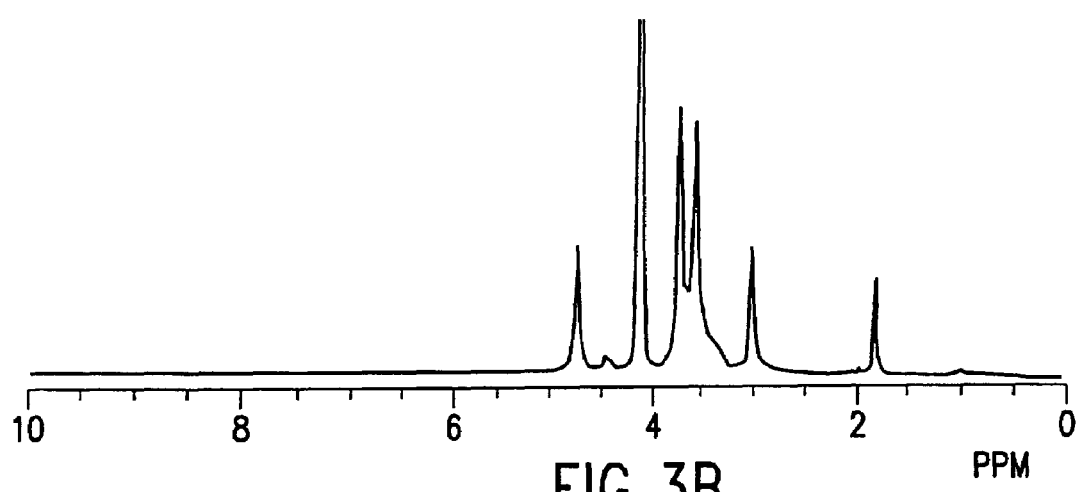
Figure 3C:
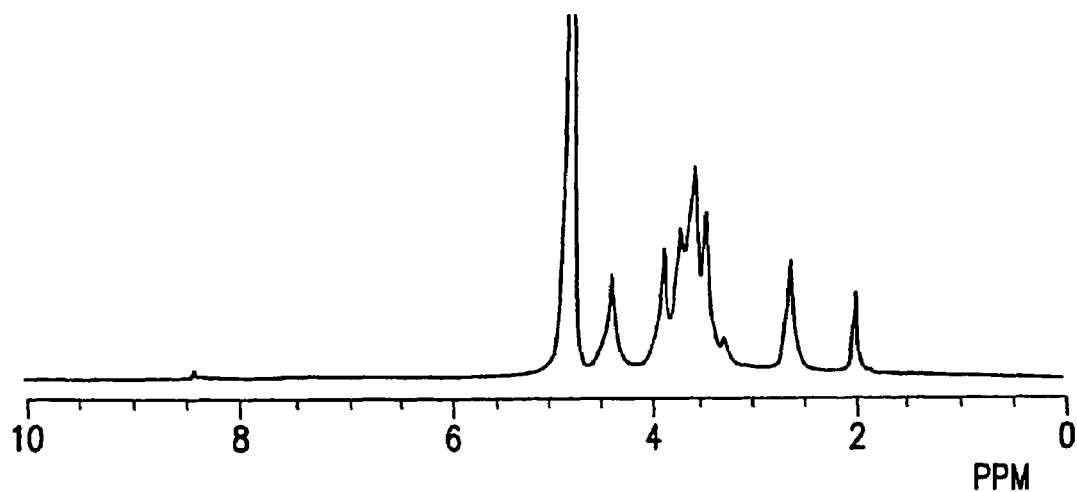

A control sample of $D_2O$-exchanged chitosan dissolved in acidic solution (acidified with HCl to a pH of 2) was prepared, and the spectrum measured. The results are shown in FIG. 3(a). Peaks were observed and assigned as follows. The 4.8 and 3.1 ppm peaks correspond to the protons on C1 and C2 in the glucosamine unit, using the numbering scheme shown in the figure. The 2.0 ppm peak corresponds to the methyl protons of the N-acetyl-glucosamine residues, and integration of the peak shows that about 10% of the sugar residues were acetylated; i.e., the chitosan sample was 90% deacetylated. The peaks between 3.4 and 4.0 ppm correspond to the $C_3$-$C_6$ protons (see, Rinaudo et al., "Substituent distribution on O,N-carboxymethylchitosan by $^1$H and $^{13}$C n.m.r.," *Int. J. Biol. Macromol.*, 14, 122-128 (1992)). The spectrum for the modified chitosan of Example 2 is shown in FIG. 3(*b*) under acidic conditions (pH 1), and in FIG. 3(*c*) under basic conditions (pH 12). At high pH, the peaks for the modified chitosan are shifted upfield (from 4.8 to 4.4 ppm for the anomeric proton, and from 3.1 to 2.6 ppm for the C2 proton). Other than these small differences, the spectra for the modified chitosan sample are essentially the same as for unmodified chitosan, indicating that the base-soluble compound is indeed a chitosan polymer.

Figure 4A:
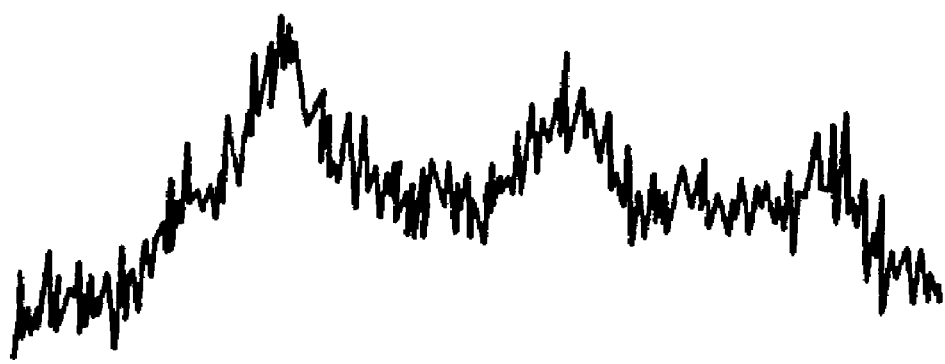
FIGS. 4(A-B) shows the features in the $^1$NMR of modified chitosan polymers in the 6.0 to 7.5 ppm region.
Figure 4B:
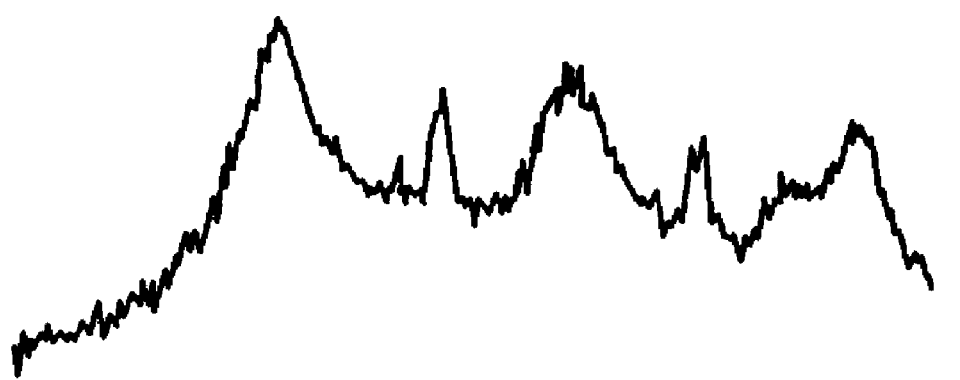

Surprisingly, no peaks corresponding to chlorogenic acid were observed on the scale shown in the figure, indicating that the degree of modification was low. FIG. 4(*a*) shows the chlorogenic acid region of the spectrum (6.0 to 7.5 ppm) of FIG. 3(*c*) with the vertical scale expanded to show less prominent features. In this region of the spectrum, one would expect to find quinoid or aromatic proton signals characteristic of a chlorogenic acid-derived moiety present on the chitosan polymer. In this expanded scale, three weak peaks are clearly visible.

NMR spectra were also recorded for the twice reacted modified chitosan of Example 3. FIG. 4(*b*) shows the same region of the spectrum, for twice-reacted modified chitosan in a pH 12 aqueous solution. As the figure shows, the quinoid or aromatic peaks are stronger in the twice-reacted chitosan (i.e., the signal to noise ratio is greater), indicating a greater extent of modification.

6.6. Example 6

Preparation and Characterization of High Viscosity Modified Chitosan Polymers High viscosity modified chitosan polymers were prepared using the same procedure as described in Example 2, except that the resultant modified chitosan polymers were not precipitated and collected, and the reagent concentrations were varied as described below. Modified chitosan polymers were prepared using p-cresol, catechol, and dopamine as the phenolic compound. Each of these modified chitosan polymers had enhanced viscosity, and the viscosity increased as the chitosan concentration increased. For example, p-cresol (18 mM) was reacted with tyrosinase (100 U/mL) in the presence of 0.48% chitosan. I.e., the amount of chitosan was three times that of Example 2, and the amount of p-cresol was adjusted to keep the phenolic compound concentration at 60% of the amino group equivalent concentration. After several hours of reaction, the solution viscosity increased dramatically, and the sample formed a highly viscous (about 400 poise) gel.

Figure 5:
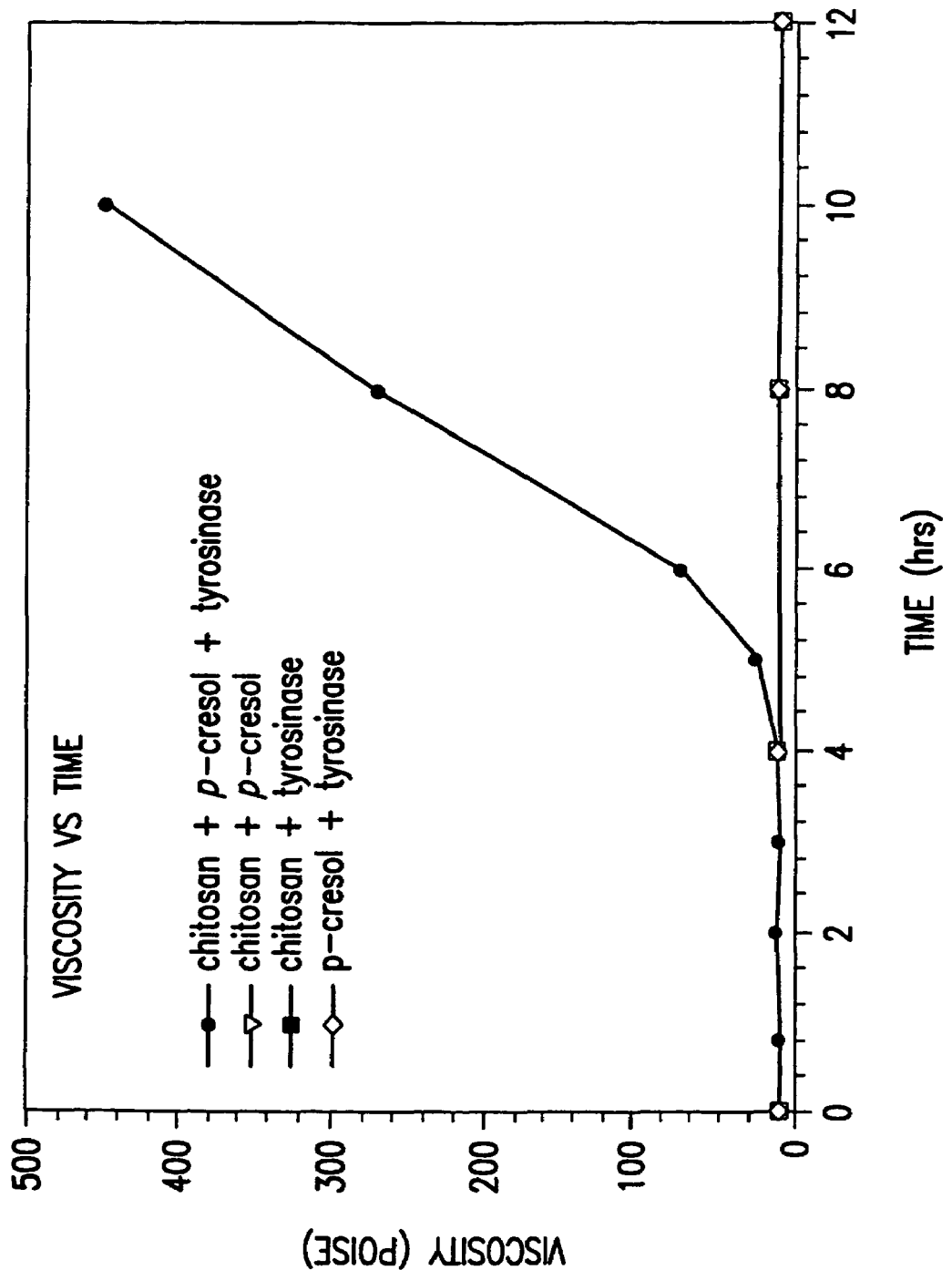
FIG. 5 shows the viscosity of a reaction solution of the present invention as a function of reaction time.

FIG. 5 shows the viscosity of a modified chitosan solution as a function of time, as the enzyme-catalyzed reaction is occurring. The phenolic compound used was p-cresol, at a concentration of 12 mM, corresponding to 60% of the equivalent amino group concentration of the 0.32% chitosan solution. Tyrosinase was used at a level of 80 U/mL. Viscosity measurements were made with a Brookfield DV-II+ viscometer with an S25 spindle at 1 rpm. The solid circles in the figure show that after about 4 hours of incubation, the solution viscosity began to increase, eventually to about 450 poise after about 10 hours. Several control solutions were also prepared and subjected to the same reaction conditions. Thus, solutions containing chitosan and p-cresol (no tyrosinase), chitosan and tyrosinase (no cresol), and p-cresol and tyrosinase (no chitosan) were used, and viscosity versus time measured for these control solutions as well. In FIG. 5, all three control solutions show the same behavior: no viscosity change is observed, and the data points in FIG. 5 overlap.

Figure 6:
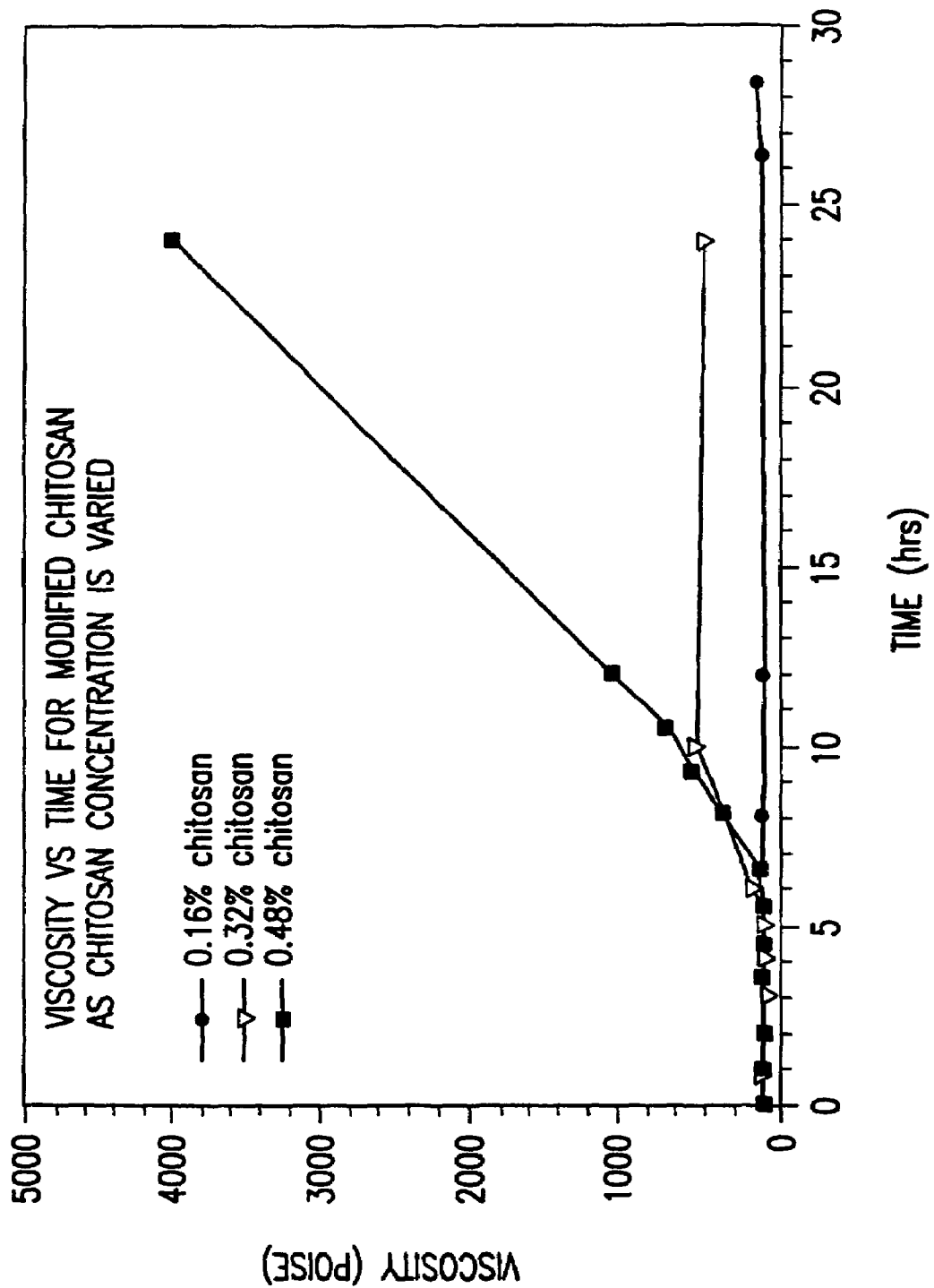
FIG. 6 shows viscosity versus time for solutions having different concentrations of chitosan.

FIG. 6 shows viscosity versus time as the concentration of chitosan was varied. The chitosan modification reactions were run as previously described, with chitosan solutions of 0.16%, 0.32% and 0.48% (equivalent amino group concentrations of 10, 20 and 30 mM). The concentration of p-cresol was adjusted to be 60% of the equivalent amino concentration in each solution (i.e., 6, 12 and 18 mM). The tyrosinase concentration was also adjusted, and values of 60, 80 and 100 U/mL were used in the 0.16, 0.32 and 0.48% solutions, respectively. Viscosity measurements were made as previously described. For the 0.16% chitosan concentration, the viscosity increased significantly, to about 40-50 poise. This increase is not shown on the scale of the Figure. The viscosity increase for the 0.32% chitosan solution is greater, showing an increase after about 5 hours to a value of about 450 poise. Note that this solution corresponds to the solution shown in FIG. 5, but the vertical scale in FIG. 6 covers a broader range. For the 0.48% chitosan solution, a modified chitosan having a viscosity of about 4000 poise after 24 hours is formed.

6.7. Example 7

Biological Degradation Of Cresol-Modified Chitosan Gels

To determine whether p-cresol-modified chitosan would be biodegradable, we incubated this gel with a commercially available chitosanase known to hydrolyze chitosan's backbone (Osswald et al., Anal. Biochem. 1992; 204:40). The modified chitosan was prepared 0.32% chitosan, 12 mM p-cresol and 80 U/ml tyrosinase and these gels were incubated in the presence and absence of chitosanase (1 U in 15 mL of gel). The viscosity of the p-cresol-modified chitosan gel was rapidly lost by incubation with chitosanase indicating that this modification does not prevent its biological degradation.

Muzzarelli and coworkers (Muzzarelli et al.; Carbohy. Polym. 1994; 24: 295) also observed that chitosan crosslinked with similar phenolic moieties were susceptible to various hydrolytic enzymes. These observations of the biological degradation of modified chitosan can be contrasted with observations that modification of cellulose by bulky substituents can disrupt its biodegradability (Sakke et al.; Progress in the enzymatic hydrolysis of cellulose derivatives. In "Cellulose Derivatives Modification, Characterization and Nanostructures" Heinze, T J, Glasser W G. ACS Symposium Series Vol. 688. American Chemical Society, Washington D.C. 1998; 201).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed is:

1. A method of producing a modified chitosan polymer or oligomer, comprising the steps of:
   (A) reacting an enzyme with at least one phenolic compound in the presence of a solubilized chitosan polymer or oligomer in a homogeneous phase, wherein said enzyme uses molecular oxygen as an oxidizing agent to oxidize said phenolic compound, and said reaction is conducted under conditions of reactivity, solubility and enzyme activity effective to maintain said reaction in a homogeneous phase and to produce an insolubilized modified chitosan polymer or oligomer; and then
   (B) solubilizing the modified chitosan polymer or oligomer.

2. The method of claim 1, wherein the enzyme is a tyrosinase, a phenol oxidase, a polyphenol oxidase, or a mixture thereof.

3. The method of claim 1, wherein the at least one phenolic compound is a phenol, a substituted phenol, a polymer having at least one phenolic moiety or tyrosine residue, or a protein having at least one phenolic moiety or tyrosine residue.

4. The method of claim 3, wherein the at least one phenolic compound is a compound having the formula

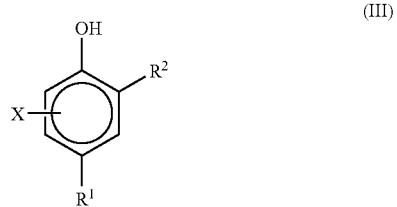

(III)

wherein $R^1$ is hydrogen, hydroxyl, alkyl or substituted alkyl, alkenyl or substituted alkenyl, cycloalkyl or substituted cycloalkyl, cycloalkenyl or substituted cycloalkenyl, aryl or substituted aryl, amino or substituted amino, carboxylic acid or carboxylic acid ester, or an aldehyde or keto group;

$R^2$ is H or OH; and

X is one or more additional substituents that can be halogen, hydroxyl, alkyl or substituted alkyl, alkenyl or substituted alkenyl, cycloalkyl or substituted cycloalkyl, cycloalkenyl or substituted cycloalkenyl, aryl or substituted aryl, amino or substituted amino, carboxylic acid or carboxylic acid ester, or two adjacent substituents which are joined to form a ring.

5. The method of claim 1, wherein the at least one phenolic compound is selected from the group consisting of phenol, 2-chlorophenol, 2,2'-dihydroxybiphenyl, 8-hydroxyquinoline, 3-amino-phenol, o-cresol, m-cresol, p-cresol, 2,3-dimethylphenol, 2-methoxyphenol, resorcinol, 1-nitrosonaphthol, hydroquinone, 4-chlorophenol, 4,4'-dihydroxybiphenyl, 2-aminophenol, 3-methoxyphenol, 1-naphthol, 4-phenylphenol, p-hydroxyphenoxyacetic acid, 5-methylresorcinol, tert-butylcatechol, catechol, methylcatechol, tyramine, dopamine, caffeic acid, hydroxycinnamic acid and chlorogenic acid.

6. The method of claim 5, wherein the at least one phenolic compound is chlorogenic acid, caffeic acid, p-cresol, catechol, dopamine or a mixture thereof.

7. The method of claim 1 wherein the at least one phenolic compound is a mixture of phenolic compounds.

8. The method of claim 1, wherein the solution is an aqueous solution or an aqueous alcohol solution.

9. The method of claim 8, wherein the solution has a pH of less than 6.5.

10. The method of claim 8, wherein the solution has a pH of at least 8.

11. The method of claim 1 wherein the modified chitosan polymer or oligomer is soluble in aqueous alkaline solution.

12. The method of claim 11, wherein the solution is an aqueous solution or an aqueous alcohol solution.

13. The method of claim 11, wherein the reaction is carried out at a pH of 5.5 to 6.5.

14. The method of claim 11, wherein the modified chitosan polymer or oligomer is soluble in aqueous alkaline solutions having a pH of at least 8.

15. The method of claim 14, wherein the modified chitosan polymer or oligomer is soluble in aqueous alkaline solutions having a pH of 8 to 14.

16. The method of claim 11, wherein the modified chitosan polymer or oligomer is soluble in aqueous acidic solutions.

17. The method of claim 11, wherein the modified chitosan polymer or oligomer is insoluble in aqueous solutions having a neutral pH.

18. The method of claim 9, wherein the modified chitosan polymer or oligomer is soluble in aqueous alkaline solutions having a pH of at least 8, soluble in aqueous acidic solutions, and insoluble in aqueous solutions having a neutral pH.

19. The method of claim 1, wherein the said method produces a modified chitosan polymer or oligomer having a higher viscosity in solution than that of the chitosan polymer or oligomer prior to said reaction.

20. The method of claim 19, wherein the viscosity of a solution of the modified chitosan polymer or oligomer is at least 1 poise.

21. The method of claim 20, wherein the viscosity of a solution of the modified chitosan polymer is at least 40 poise.

22. The method of claim 21, wherein the viscosity of a solution of the modified chitosan polymer or oligomer is at least 400 poise.

23. A method of producing a modified chitosan polymer or oligomer, comprising the steps of:
   (a) providing a chitosan polymer or oligomer solubilized in a solution;
   (b) reacting an enzyme with at least one phenolic compound in the presence of said solubilized chitosan polymer or oligomer in a homogeneous phase, wherein said reaction is conducted under conditions of reactivity, solubility and enzyme activity effective to maintain said reaction in a homogeneous phase and to produce an insolubilized modified chitosan polymer or oligomer; and then solubilizing said produced modified chitosan polymer or oligomer; and then
   (c) additionally reacting an enzyme with at least one phenolic compound in the presence of said solubilized modified chitosan polymer or oligomer in a homogeneous phase, wherein said enzyme uses molecular oxygen as an oxidizing agent to oxidize said phenolic compound, and said additional reaction is conducted under conditions of reactivity, solubility and enzyme activity effective to maintain said additional reaction in a homogeneous phase and to produce a further modified chitosan polymer or oligomer.

24. The method of claim 23, which further comprises repeating step (c) to further modify the further modified chitosan polymer.

25. The method of claim 23, wherein the reaction of step (b) is carried out at a pH of 5.5 to 6.5.

26. The method of claim 23, wherein the reaction of step (c) is carried out at a pH greater than 6.5.

27. The method of claim 26, wherein the reaction of step (c) is carried out at a pH of at least 8.

28. The method of claim 1, further comprising further reacting the modified chitosan polymer or oligomer.

29. The method of claim 28, wherein said further reacting is performed in an alkaline solution.

30. The method of claim 28, wherein said further reacting comprises reacting an enzyme with at least one phenolic compound in the presence of the modified chitosan polymer or oligomer to produce a further modified chitosan polymer or oligomer.

31. The method of claim 28, wherein said further reacting comprises reacting an attached moiety of the modified chitosan polymer or oligomer, the attached moiety being derived from at least one of the enzyme and the phenolic compound.

32. The method of claim 1, wherein said reacting comprises leaving an unmodified portion of the chitosan polymer or oligomer unreacted, and wherein the method further comprises separating the unmodified portion and the modified chitosan polymer or oligomer from one another.

33. The method of claim 1, wherein the phenolic compound is selected from the group consisting of a phenolic protein and a phenolic peptide.

34. The method of claim 23, wherein the at least one phenolic compound reacted in step (b) is different from the at least one phenolic compound further reacted in step (c).

35. The method of claim 23, wherein said reacting step (b) comprises leaving an unmodified portion of the chitosan polymer or oligomer unreacted, and wherein the method further comprises separating the unmodified portion and the modified chitosan polymer or oligomer from one another prior to said further reacting step (c).

36. The method of claim 23, wherein at least one phenolic compound is selected from the group consisting of a phenolic protein and a phenolic peptide in the presence of a chitosan polymer or oligomer.

* * * * *